United States Patent
Anderson et al.

(10) Patent No.: US 10,674,898 B2
(45) Date of Patent: Jun. 9, 2020

(54) DISPOSABLE SUCTION VALVE FOR AN ENDOSCOPE

(71) Applicant: MEDIVATORS INC., Minneapolis, MN (US)

(72) Inventors: Bob Anderson, Montgomery, TX (US); Christopher Steven Adams, Montgomery, TX (US); Don Byrne, Montgomery, TX (US)

(73) Assignee: Medivators Inc., Minneapolis, MN (US)

(*) Notice: Subject to any disclaimer, the term of this patent is extended or adjusted under 35 U.S.C. 154(b) by 62 days.

(21) Appl. No.: 15/446,649

(22) Filed: Mar. 1, 2017

(65) Prior Publication Data

US 2017/0172391 A1 Jun. 22, 2017

Related U.S. Application Data

(63) Continuation of application No. 13/989,573, filed as application No. PCT/US2011/062594 on Nov. 30, 2011, now Pat. No. 9,585,545.

(Continued)

(51) Int. Cl.
*A61B 1/00* (2006.01)
*A61B 1/015* (2006.01)

(52) U.S. Cl.
CPC ............ *A61B 1/015* (2013.01); *A61B 1/0011* (2013.01); *A61B 1/00068* (2013.01); *A61B 1/00094* (2013.01); *Y10T 29/49412* (2015.01)

(58) Field of Classification Search
CPC ... A61B 1/015; A61B 1/00094; A61B 1/0011; A61B 1/00068; Y10T 29/49412
See application file for complete search history.

(56) References Cited

U.S. PATENT DOCUMENTS 4,261,343 A * 4/1981 Ouchi ................ A61B 1/12
                                                        600/158
4,361,138 A    11/1982 Kinoshita
                (Continued)

FOREIGN PATENT DOCUMENTS

EP      0055394         3/1985
EP      1099393 A1      5/2001
        (Continued)

OTHER PUBLICATIONS

International Search Report and Written Opinion by the International Searching Authority Filed in Application No. PCT/US2011/062594 dated Nov. 30, 2011 and dated Mar. 29, 2012.

(Continued)

*Primary Examiner* — Timothy J Neal
(74) *Attorney, Agent, or Firm* — Sorell, Lenna & Schmidt, LLP; William D. Schmidt, Esq.

(57) ABSTRACT

A disposable suction valve is provided. In some embodiments, the disposable suction valve may include a stem providing an air passage through the stem, a spring, a spring stanchion cup, and a boot. A method for manufacturing a disposable suction valve may include several steps. A stem and spring stanchion cup are molded, and a bottom end of the stem is placed through the center of a spring. The bottom end of the stem is placed through a stem opening in the spring stanchion cup, and the tabs or the spring stanchion cup are placed into recessed apertures of the stem. The boot may be over-molded on the spring stanchion cup or molded and placed onto the spring stanchion cup.

23 Claims, 8 Drawing Sheets

Related U.S. Application Data

(60) Provisional application No. 61/418,089, filed on Nov. 30, 2010.

(56) References Cited

U.S. PATENT DOCUMENTS

| | | | |
|---|---|---|---|
| D300,361 S | 3/1989 | Tokarz | |
| 4,900,305 A | 2/1990 | Smith | |
| 5,391,145 A * | 2/1995 | Dorsey, III | A61M 1/0064 137/596.2 |
| 5,522,796 A | 6/1996 | Dorsey, III | |
| 5,840,016 A | 11/1998 | Kitanao et al. | |
| 5,871,441 A * | 2/1999 | Ishiguro | A61B 1/00068 600/133 |
| 5,876,326 A | 3/1999 | Takamura et al. | |
| 6,346,075 B1 * | 2/2002 | Arai | A61B 1/00068 600/159 |
| D473,646 S | 4/2003 | Baillargeon | |
| D473,941 S | 4/2003 | Cise et al. | |
| D546,946 S | 7/2007 | Blake et al. | |
| 2004/0238014 A1 * | 12/2004 | Halstead | A61B 1/00068 134/32 |
| 2006/0041190 A1 | 2/2006 | Sato | |
| 2012/0088975 A1 | 4/2012 | Morimoto | |
| 2012/0091092 A1 | 4/2012 | Adams et al. | |
| 2013/0303844 A1 | 11/2013 | Grudo et al. | |

FOREIGN PATENT DOCUMENTS

| | | |
|---|---|---|
| JP | 58-010031 A | 1/1983 |
| JP | S61-124602 A | 8/1986 |
| JP | S62-133929 A | 6/1987 |
| JP | 62-189041 A | 8/1987 |
| JP | H8-215137 A | 2/1995 |
| JP | 08-266461 A | 10/1996 |
| JP | 09-122069 A | 5/1997 |
| JP | 1998-248791 A | 9/1998 |
| JP | H10-24879 A | 9/1998 |
| JP | 2000217777 A | 8/2000 |
| JP | 2002-306405 A | 10/2002 |
| JP | 2002306405 A | 10/2002 |
| JP | 2003-310542 A | 5/2003 |
| JP | 2004-169805 A | 6/2004 |
| JP | 2005261512 A | 9/2005 |
| JP | 2006-55447 A | 2/2006 |
| JP | 2006-175175 A | 7/2006 |
| JP | 2007-185276 A | 7/2007 |
| JP | 4242142 B | 3/2009 |
| JP | 4583915 B2 | 11/2010 |
| JP | 4589315 B | 11/2010 |
| WO | 2009-016352 A2 | 2/2009 |

OTHER PUBLICATIONS

Supplementary Partial European Search Report of the European Patent Office dated Nov. 22, 2016 and dated Dec. 2, 2016 of European Patent Application No. EP 11 84 5027 filed on Nov. 30, 2011.

Supplementary European Search Report dated Apr. 25, 2017 and dated May 9, 2017 of European Patent Application No. EP 11 84 5027 filed on Nov. 30, 2011.

European Search Report of the European Searching Authority dated Mar. 15, 2016 of European Patent Application No. EP 11 84 5986 filed Nov. 30, 2011.

Olympus Operation Manual, dated 2003, 102 pages, entire document.

Third party submission filed on Jul. 17, 2014 in U.S. Appl. No. 13/989,573, filed Jul. 17, 2013.

Third party submission filed on Jul. 17, 2014 in U.S. Appl. No. 13/989,649, filed Jul. 17, 2013.

Photo of Olympus suction valve MH-443 from internet website www.partsfinder.com, website visited Jan. 8, 2019 at https://www.partsfinder.com/parts/olympus-america-inc/MH443.

Photo of Olympus air/water valve MH-438 from internet website www.dotmed.com, website visited Jan. 8, 2019 at https://www.dotmed.com/listing/endoscope/olympus/mh-438/2101261.

Pentax Owner's Manual Pentax Video GI Scopes EG-290Kp, EC-380LKp, Nov. 2009.

Photos of Pentax OF-B120 Suction Control Valve, Pentax OF-B188 Air/Water Feeding Valve and Pentax OF-B121 Air/Water Valve, 2009.

Photos of Olympus Suction Valve MH-443 with parts separated, 2003.

Photos of Olympus Air/Water Valve MH-438 with parts separated, 2003.

* cited by examiner

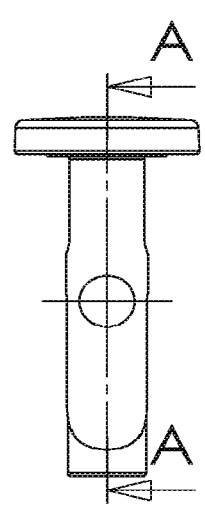
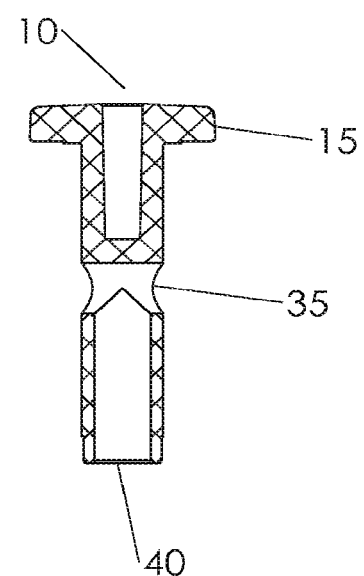
FIGURE 4A
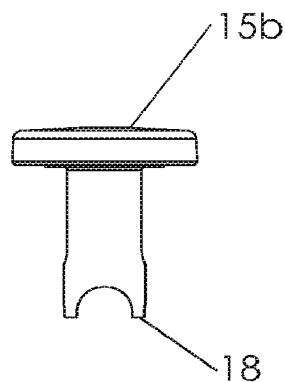
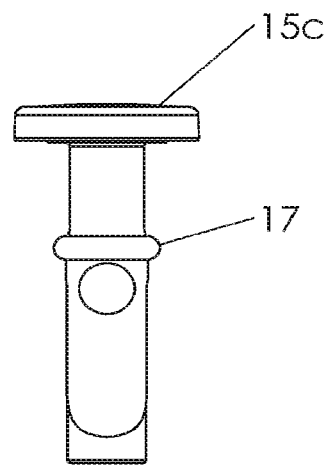
FIGURE 4B          FIGURE 4C

DISPOSABLE SUCTION VALVE FOR AN ENDOSCOPE

This application claims the benefit of the filing date of U.S. Provisional Patent Application Ser. No. 61/418,089, filed on Nov. 30, 2010. This entire disclosure is hereby incorporated by reference into the present disclosure.

FIELD

This application relates to medical instrument systems. More particularly, suction valves for endoscopes and methods for manufacturing such valves.

BACKGROUND

Endoscopes are well-known in the art and are commonly used for numerous medical procedures. A control section of an endoscope may include a suction cylinder, air/water cylinder, and the like. Valves may be inserted into these cylinders to control various functions of the endoscope.

For example, a suction valve for an endoscope may be inserted into a suction cylinder of the endoscope to provide suction to the endoscope. When the suction valve is in a normal position, air flow from the distal tip of the endoscope is blocked by the valve. When suction is desired, an operator engages the suction valve (e.g. by depressing the valve) to open the suction channel to create negative pressure that draws air or fluid into the opening of the instrument channel of the endoscope. When the operator releases the suction valve, the valve returns to its normal position blocking air flow and stops the suctioning.

After each use, an endoscope may undergo cleaning, disinfection, sterilization, and the like to prevent the spread of disease, germs, bacteria, illness, and the like. Many components of an endoscope may be reusable, such as a suction valve, and must also be cleaned, disinfected, and/or sterilized between uses. Unfortunately, there is usually a great expense associated with maintaining sterility of the equipment. Additionally, there exists significant difficulty for access to the suction valve features to properly disinfect/clean the device.

Reusable suction valves may be assembled from the combination of several metal, plastic, and/or rubber components. As such, there is significant cost associated with the manufacturing of reusable suction valves.

Disposable suction valves obviate the need for cleaning, disinfection, and sterilization, thereby eliminating the cost of repeated cleaning, disinfection, and sterilization. Additionally, disposable suction valves do not require expensive materials to be utilized to manufacture the valves, thereby eliminating the high cost of manufacturing suction valves from expensive materials.

Thus, there is a need to develop new disposable suction valves and methods that reduce or eliminate the need for repeated cleaning, disinfection, and sterilization and reduce or eliminate the risk of infecting the patient. Suction valves that have reduced risk of clogging would also be very useful.

SUMMARY

New devices and methods are provided that reduce or eliminate the risk of contaminating the endoscope and reduce or eliminate the risk of infecting the patient. The suction valve provided is lightweight, easy to use and, in some embodiments, improves suction efficiency.

Various embodiments of a disposable suction valve for an endoscope are discussed herein, including manufacturing processes for disposable suction valves.

In some embodiments, a disposable suction valve may include a main stem providing an air passage through the center bore of the main stem. The disposable suction valve may also include a spring stanchion cup and a spring. A boot may be over-molded on the exterior of the spring stanchion cup.

In some embodiments, the method for manufacturing a disposable suction valve may include several steps. A main stem and spring stanchion cup are molded. The bottom end of the main stem is placed through the center of the spring and spring stanchion cup. A boot may be over-molded to the spring stanchion cup to complete the disposable suction valve.

In some embodiments, there is a suction valve assembly comprising: a stem comprising at least one recess and/or projection disposed on the stem, a first opening disposed along a longitudinal axis of the stem, and a second opening disposed transverse to the first opening, the first and second openings for allowing passage of air and/or fluid; a spring stanchion comprising at least one recess and/or projection configured to attach to the recess and/or projection of the stem; the spring stanchion comprising an opening configured to receive the stem and allow movement of the stem in an upward and downward position; and a spring configured to contact the spring stanchion and the stem.

In some embodiments, a stem is provided, which significantly reduces the distal section of the stem below the transverse port of the stem.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 4a illustrates a side view and a cross sectional view of an embodiment of a stem rotated about 90 degrees;

FIG. 4b illustrates an embodiment of alternative implementation of a stem;

FIG. 4c illustrates an embodiment of another implementation of a stem;

Figure 1:
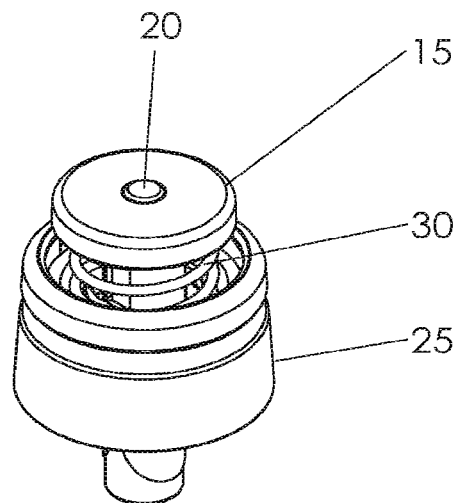
FIG. 1 illustrates an isometric view of an embodiment of a disposable suction valve.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

It is noted that, as used in this specification and the appended claims, the singular forms "a," "an," and "the," include plural referents unless expressly and unequivocally limited to one referent. Thus, for example, reference to "a stanchion cup" includes one, two, three or more stanchions cups.

We refer now to the drawings wherein depicted elements are not necessarily shown to scale and wherein like or similar elements are designated by the same reference numeral through the several views.

Referring to the drawings in general, it will be understood that the illustrations are for the purpose of describing particular embodiments of the disclosure and are not intended to be limiting thereto.

While most of the terms used herein will be recognizable to those of ordinary skill in the art, it should be understood that when not explicitly defined, terms should be interpreted as adopting a meaning presently accepted by those of ordinary skill in the art.

Figure 2:
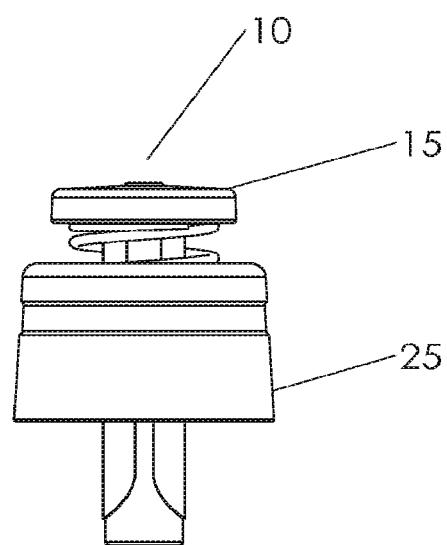
FIG. 2 illustrates a side view of an embodiment of a disposable suction valve.

FIG. 1 is an isometric view of a disposable suction valve 10. FIG. 2 is a side view of an illustrative embodiment of a disposable suction valve 10. While the disposable suction valve 10 shown is suitable for use with Olympus® endoscopes, other embodiments of disposable suction valves may be suitable for use with other types of endoscopes, such as Pentax®, Fujinon®, or the like. As such, the embodiments discussed herein may be modified to accommodate other types and/or brands of endoscopes.

Disposable suction valve 10 may provide a stem 15, stem insert 20, boot 25, spring cup/stanchion (not shown) and spring 30. One or more components of the disposable suction valve may comprise disposable material, including, but not limited to polyurethane, polyurea, polyether(amide), PEBA, thermoplastic elastomeric olefin, copolyester, and styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), ABS, MABS, silicone, or the like or combinations thereof. Stem 15 and stem insert 20 may be formed from a suitable material or combination of material(s), such as plastic, polymeric material(s), or the like. Stem insert 20 may be color coded (e.g. black, red, green, etc.) to indicate the type of valve or that the valve is a suction valve. In other embodiments, stem insert 20 may be omitted or color coding may be provided by another means (e.g. painting).

Boot 25 may be formed from a suitable material, such as for example, polyurethane, polyurea, polyether(amide), PEBA, thermoplastic elastomeric olefin, copolyester, and styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), or the like or combinations thereof.

In one embodiment, boot 25 may be made from a pliable material for ease of assembly e.g., a material that allows boot 25 to be slid over spring stanchion cup (not shown) during assembly and to seal off the suction in the circuit. In other embodiments, boot 25 may be over-molded onto the spring stanchion cup. Spring 30 may be formed from a suitable material, such as corrosion resistant metal, polyurethane, polyurea, polyether(amide), PEBA, thermoplastic elastomeric olefin, copolyester, and styrenic thermoplastic elastomer, carbon fiber, glass fiber, ceramics, methacrylates, poly (N-isopropylacrylamide), PEO-PPO-PEO (pluronics), rubber, plastic, or the like or combinations thereof.

While a spring 30 is shown in FIG. 1, it will be understood that any resilient member (e.g., a member that resumes its original shape or position after being compressed) can be used. A resilient member can include, for example, a spring, plastic, rubber or other elastic member that allows its original shape or position after being compressed.

The air used for suction in combination with the device can be filtered using an inline air filter assembly having a porous medium to filter air. This filter may be disposed in the air path exterior of it within the suction channel. The porous media can be made of polyethersulfone, PTFE, a PVC, acrylic copolymer, polysulfone, polyvinylidene fluoride, cellulose acetate, cellulose nitrate, mixed esters of cellulose, nylon, polyamide or a combination thereof. The filter can be microporous, and the mean pore size of the media is from about 0.2 micron to about 150 microns. In some embodiments, the filter can have a mean pore size of about 0.22 micron to about 0.8 micron.

In contrast, the stem of a re-usable suction valve may be formed from one or more components made of a material that is suitable for repeated cleaning, disinfection, and sterilization, such as stainless steel or the like. While this material allows a re-usable suction valve to be repeatedly cleaned, disinfected, and sterilized for re-use, such material may be costly; is difficult to properly clean; requires more components; requires additional manufacturing and assembly steps; requires more costly manufacturing processes; and the like. In addition to being more costly to manufacture than a disposable suction valve, a re-usable suction valve also requires equipment and materials that are utilized to repeatedly clean, disinfect, and sterilize the valve.

The disposable suction valve of the current application, in some embodiments and as shown in FIG. 4B, improves suction, reduces or eliminates leaks and/or fluid going into and out of unwanted areas of the valve or in unwanted areas of the medical instrument. The disposable suction valve of the current application, in some embodiments, reduces or eliminates debris from clogging the valve.

In some embodiments, unlike the non-disposable seven-component suction valves in the prior art, the disposable suction valve of the current application, comprises four components: a stem 15, boot 25, spring cup/stanchion (not shown) and spring 30. In some embodiments, unlike the non-disposable seven-component suction valves in the prior art, the disposable suction valve of the current application, comprises five components: a stem 15, boot 25, spring cup/stanchion (not shown), spring 30, and stem insert 20.

In some embodiments, the difference from the disposable suction valve of the current application and the prior is that in the prior art valve construction, the prior art valve has a stem (with a threaded button head end) plus a metal backing plate (to thread onto stem and offer a secure joint for the plastic button head) and a plastic button head. In the disposable suction valve of the current application, in some embodiments, the stanchion cup is molded and then the boot is overmolded onto this piece. Accordingly, in some embodiments, the stanchion cup is monolithic with the boot (e.g., they are one piece) and therefore, the manufacturing process is simpler. Therefore, the disposable suction valve of the current application can be easier to manufacture and there is less chance of the components malfunctioning when compared to prior art non-disposable seven-component suction valves.

Figure 3:
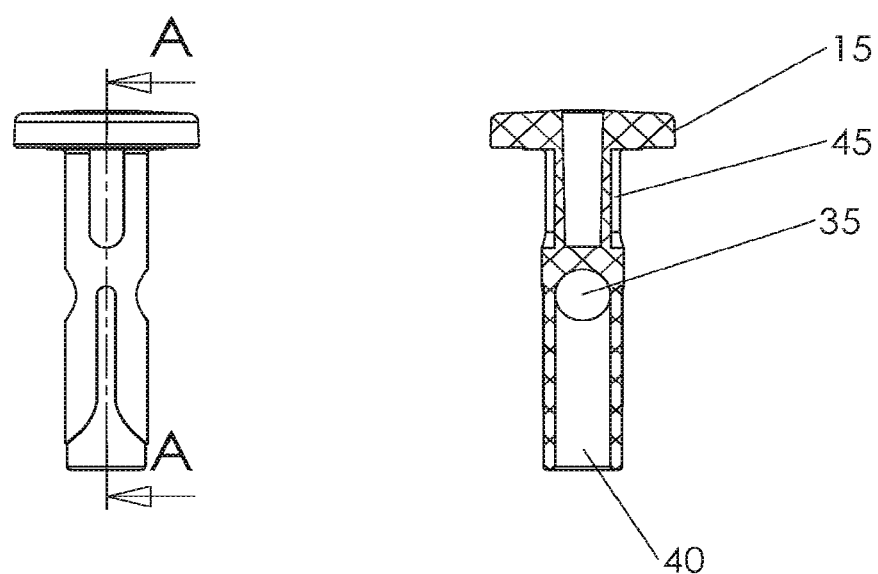
FIG. 3 illustrates a side view and a cross sectional view of an embodiment of a stem.

FIG. 3 and FIG. 4a show cross sectional views of illustrative embodiments of stem 15 rotated 90 degrees. FIG. 3 and FIG. 4a also show stem 15 in a side view along longitudinal axis AA. Stem 15 is a single molded component of disposable suction valve 10. Stem 15 provides openings 35 and 40 passing through the stem. Fluid may pass horizontally through one side of opening 35 and vertically through opening 40. The stem 15 is symmetrical for ease of use. Openings 35 and 40 may allow air or fluid to pass through the instrument channel of an endoscope when a suction valve is actuated. Recessed apertures 45 may be utilized to secure a spring stanchion cup or flange to stem 15. In some embodiments of stem 15, the stem diameter may be precisely controlled to assure an air tight or nearly air tight seal within the suction cylinder/port of an endoscope.

FIG. 4b is an illustrative embodiment of alternative implementation of a stem 15b. Stem 15b has a reduced stem length and includes points 18. Suction valves may clogged due to debris from the body that "plugs" the vertical and horizontal passages of the suction valve stem. By reducing or eliminating, in essence, the "tube" portion of the stem below the opening in the stem, this clogging condition can be drastically reduced or eliminated. Points 18 minimize the contact between stem 15b and the interior of the suction cylinder of the endoscope, thereby reducing or eliminating the chances of debris clogging in the stem 15b jamming in the endoscope. Points 18 are positioned at a distal end of stem 15.

By reducing the stem length suction efficiency is improved and the potential for suction valve clogging is reduced or eliminated. In some embodiments, the shorter stem allows the user to press less on the valve in a downward direction to align an opening with the suction channel (not shown). In this way, debris and/or fluid is prevented from clogging the suction channels as the distance to align the suction channel with the opening is shorter. In some embodiments, the stem length is reduced by 10%, 20%, 30%, 40%, 50%, or 60% compared to stems that are full length (e.g., full length stems can be 0.95 of an inch).

FIG. 4c is an illustrative embodiment of another implementation of a stem 15c. Stem 15c may include an O-ring 17 or any other suitable alternative sealing method, which may be over-molded on stem 15c or placed on stem 15c during assembly. O-ring 17 may seal suction cylinder to prevent air and/or fluids from escaping through suction valve 15c. O-ring 17 may also include, in some embodiments, mold design considerations that provide a substantially or perfectly cylindrical stem and/or fully concentric configuration in order to provide an air tight seal in the endoscope port.

It will be understood that the seal can be any member suitable for sealing a portion of the stem. The seal can be permanently attached to the stem, such as for example, by over-molding so that is a raised member. In some embodiments, the seal can be removably attached to the stem, such as for example, by sliding it on the stem. Like other components of the suction valve, the seal can comprise polyurethane, polyurea, polyether(amide), PEBA, thermoplastic elastomeric olefin, copolyester, and styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), ABS, MABS, silicone or the like or combinations thereof.

Figure 5:
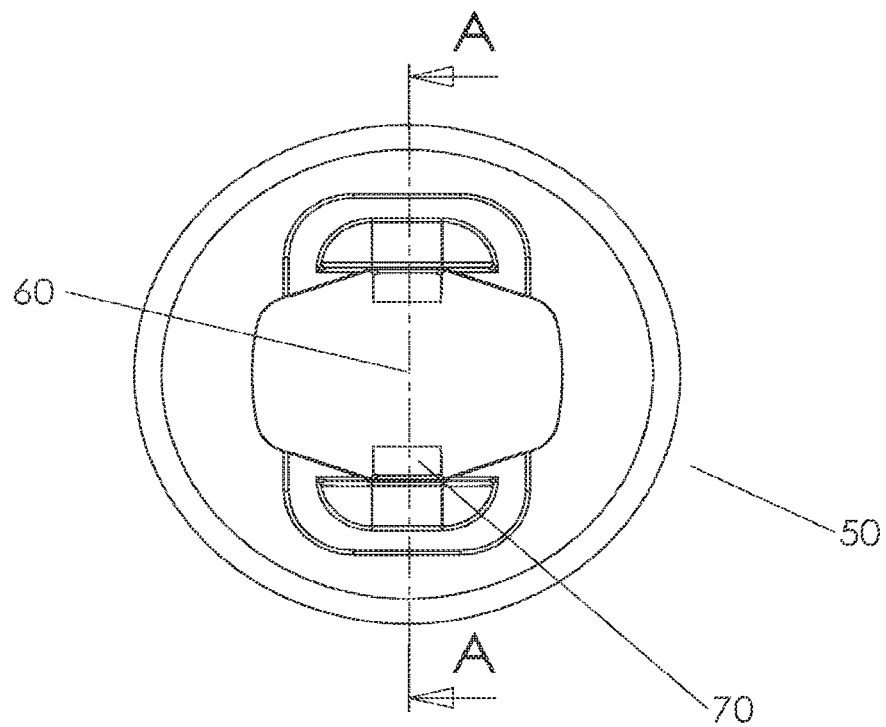
FIG. 5 illustrates a top view of an embodiment of a spring cup or stanchion cup.
Figure 6:
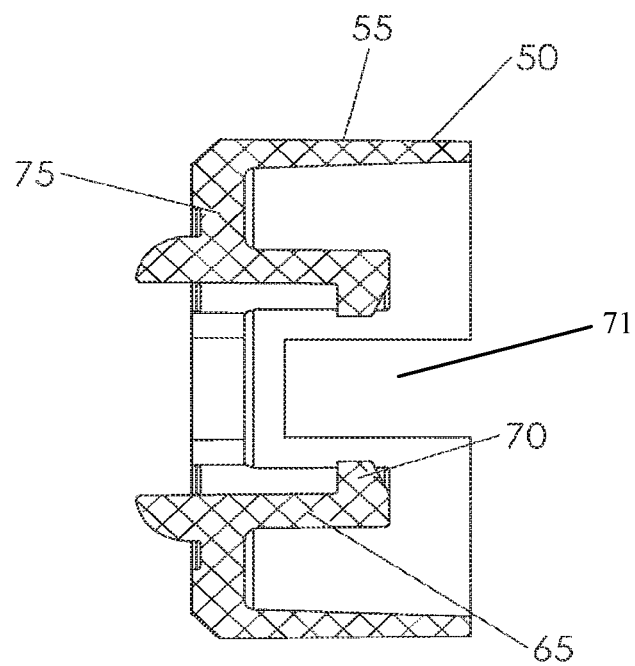
FIG. 6 illustrates a cross sectional view of an embodiment of a spring cup or stanchion cup.

Referring to FIG. 5 and FIG. 6, FIG. 5 is top view of an illustrative embodiment of a spring stanchion cup 50. FIG. 6 is a cross section view of an illustrative embodiment of spring stanchion cup 50. Spring stanchion cup 50 includes outer ring 55, stem opening 60, extensions 65, tabs 70, and diaphragm 75. Outer ring 55 shown in FIG. 6 provides a generally cylindrical ring body for spring stanchion cup 50. Stem opening 60 provides an opening for receiving stem 15. Extensions 65 extend up from diaphragm 75 of spring stanchion cup 50. Extensions 65 extend a predetermined distance from diaphragm 75 and work in conjunction with recessed apertures 45 of FIG. 3 to limit how far stem 15 travels when the disposable suction valve (10 of FIG. 3) is actuated or released. Tabs 70 may protrude from the top of extensions 65 towards stem opening 60. When disposable suction valve 10 is assembled, a spring is placed between stem 15 and diaphragm 75 of spring stanchion cup 50. Tabs 70 of spring stanchion cup 50 are placed into recessed apertures 45 of stem 15, thereby securing spring stanchion cup 50 to stem 15. Spring 30 maintains disposable suction valve 10 in an un-actuated position, unless an operator depresses disposable suction valve 10. In some embodiments, spring stanchion cup 50 may have one or more, recesses, such as for example, cut outs 71 that can be any shape (circular, square, triangle, etc.) to allow for bonding to a boot, such as for example, boot 25 shown in FIG. 1 and FIG. 2.

While a spring stanchion cup 50 is shown in FIGS. 5 and 6, it will be understood that any flange can be used to hold a portion of the resilient member (e.g., spring, rubber, etc.) in position that allows the resilient member to return to its original shape or position after being compressed.

In some embodiments, spring stanchion cup 50 the cut outs 71 are configured to allow for bonding to an over molded boot in a subsequent over molding operation. In some embodiments, the cutouts 71 are configured to mate with corresponding projections, recesses or cutouts of the stem and/or boot to lock the spring stanchion cup 50 to the stem and/or boot. In this way the components are attached to each other. In some embodiments, the boot 25 creates the seal and, among other things, enhances suction as compared to prior art suction valves by about 10%, 15%, 20%, 25%, 30%, 35%, 40%, 45%, 50%, 55%, or 60% or more, depending on composition of the bodily fluid suctioned. For example, bodily fluid (e.g., waste, blood, etc.) having a low viscosity like water can be suctioned more than about 12% with the current disposable suction valve while higher viscosity bodily fluids that are thicker can be suctioned more than about 40% with the current disposable suction valve.

In some embodiments, the concentricity of the stem is used to optimize suction. Therefore, manufacturing methodology that enhances concentricity of the stem can provide optimum suction capability.

Figure 7:
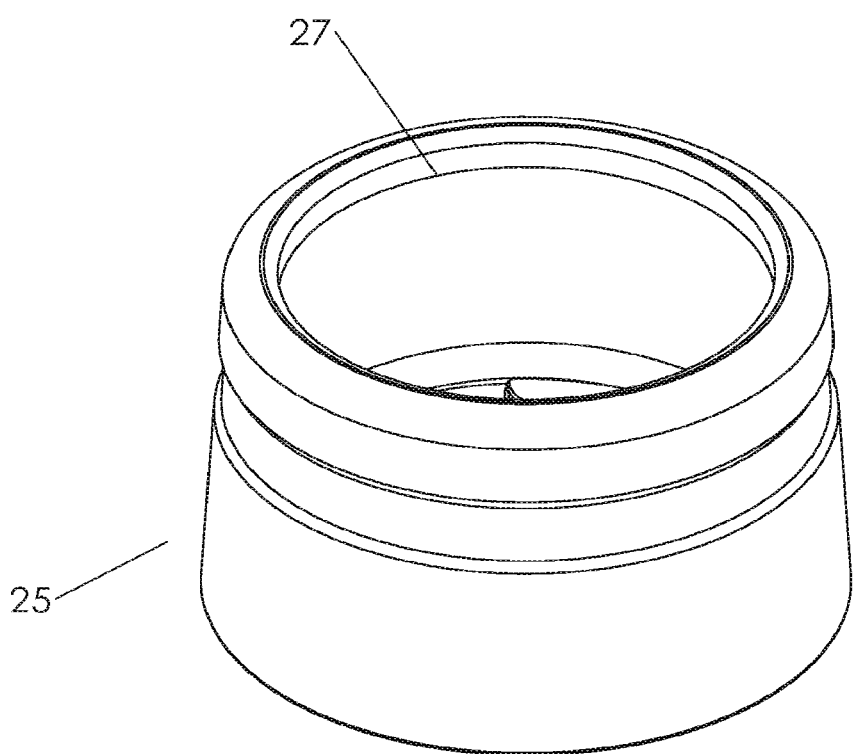
FIG. 7 illustrates an isometric view of an embodiment of a boot.
Figure 8:
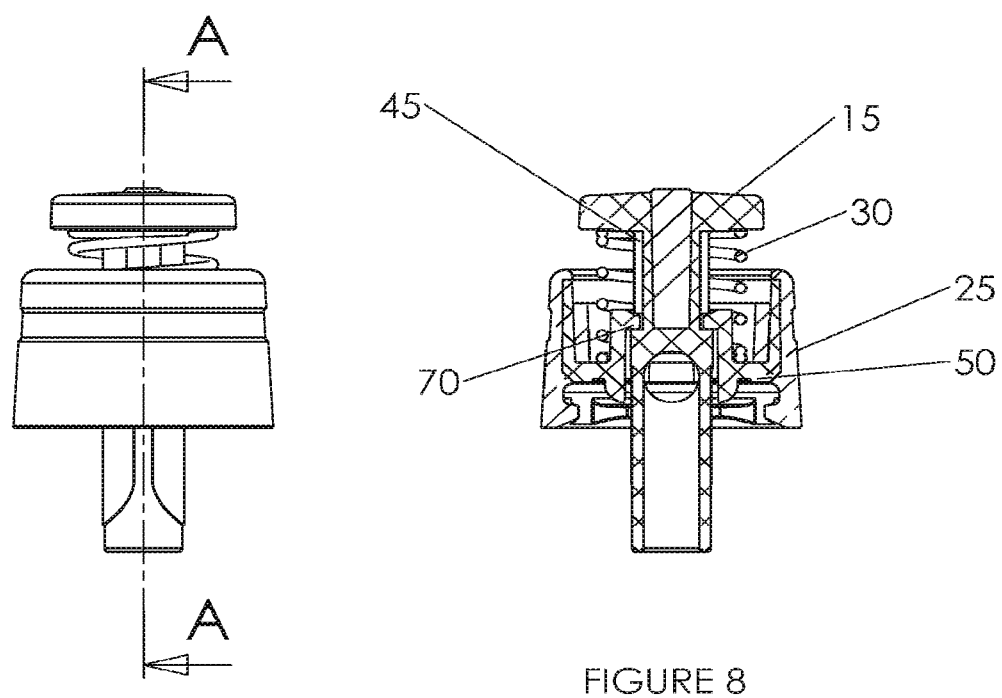
FIG. 8 illustrates a cross sectional view of an embodiment of a disposable suction valve.

FIG. 8 shows a cross sectional view and side view of an illustrative embodiment of an assembled disposable suction valve 10. Stem 15 extends through spring 30 and spring stanchion cup 50. Boot 25 is over-molded or placed over spring stanchion cup 50. Boot 25 provides a sealing ledge 27 that seals off the suction port in the endoscope. For example, the top of stem 15 engages sealing ledge 27 when disposable suction valve 10 is depressed. In an illustrative embodiment shown in FIG. 7, boot 25 provides a sealing ledge 27 that seals off the suction port in the endoscope. Note that sealing ledge 27 may be placed at any suitable position on boot 25. Further, sealing ledge 27 may alternatively be disposed on spring stanchion cup 50. For example, a sealing ledge on the boot or spring stanchion cup may create a seal against stem 15, suction cylinder, a portion of the endoscope, or the like. Tabs 70 of spring stanchion cup 50 reside in recessed apertures 45 of stem 15. Recessed apertures 45 allow the restricted movement of stem 15 up and down on spring stanchion cup 50. The recessed apertures 45, in some embodiments, can be disposed on all or a portion of the stem 15. In some embodiments, the recessed apertures 45 can be disposed on all or a portion of opposed surfaces of the stem 15.

As shown, spring 30 maintains stem 15 in its upper position, but recessed apertures 45 and tabs 70 prevent stem 15 from being separated from spring stanchion cup 50. When disposable suction valve 10 is actuated, spring 30 is compressed and stem 15 moves further down into spring stanchion cup 50. Recessed apertures 45 limit how far down stem 15 may travel because tabs 70 will eventually come in contact with the top part of stem 15. In some embodiment, the top part of stem 15 can also be referred to as a button head or button cap.

Figure 9A:
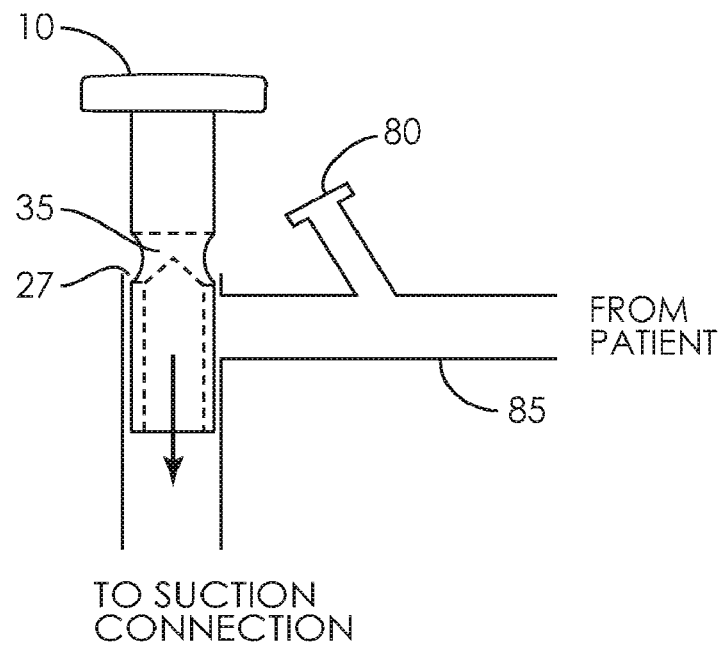
FIGS. 9a and 9b illustrate embodiments of the general operation of a disposable suction valve in a medical instrument, such as for example, an endoscope.
Figure 9B:
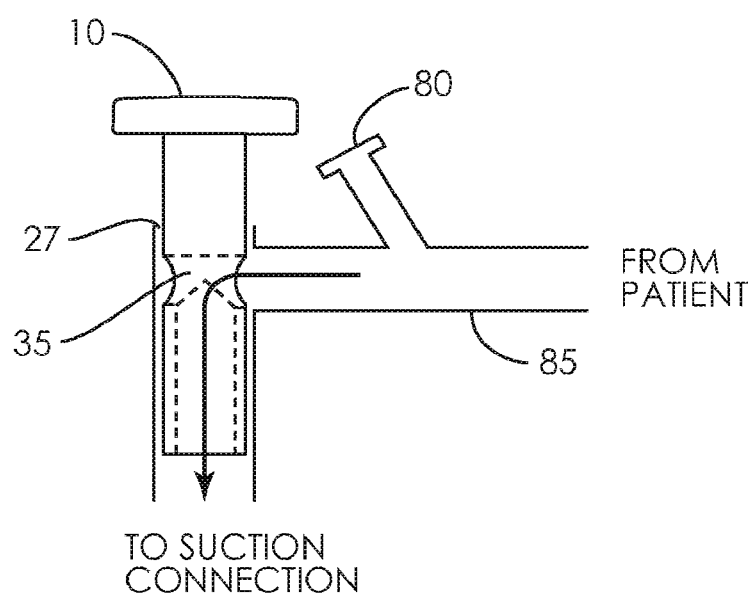

FIGS. 9a and 9b are illustrative embodiments of the general operation of a disposable suction valve 10 in an endoscope. Disposable suction valve 10 may be placed into the suction cylinder of an endoscope. The suction channel 85 of the endoscope is linked to the instrument channel 80 and leads to the distal end of an endoscope or leads toward the patient. The endoscope may be connected to a suction pump or the like to create negative pressure in the suction channel when a suction valve is actuated. In an un-actuated position shown in FIG. 9a, opening 35 is out of position with suction channel 85, thereby preventing the suction pump from creating negative pressure in the suction channel 85. Suction valve 10 has not created a seal against sealing ledge 27 in an un-actuated position, which may allow air to enter through suction cylinder/port of the endoscope through suction valve 10.

For example, disposable suction valve 10 when spring 30 is not compressed, shown in an un-actuated position in FIG. 8, may allow air to enter through suction valve 10. Note that stem 15 does not create a seal against spring stanchion cup 50, and stem 15 does not create a seal against the cylinder wall of the suction cylinder of the endoscope in the non-actuated position. When an operator actuates disposable suction valve 10 (e.g. depressing stem 15 and compressing spring 30), opening 35 moves into position with the suction channel 85 from the distal end of the endoscope or from the patient as shown in FIG. 9b. Further, disposable suction valve 10 creates a seal between the stem 15 and sealing ledge 27 when actuated.

By aligning opening 35 with the suction pathway from the patient and sealing the suction cylinder of the endoscope, the negative pressure created by a suction pump or the like cause flow from the distal end of the endoscope towards the suction connection as shown in FIG. 9b. As a result, air and/or fluid may be suctioned from the distal end of the endoscope when disposable suction valve 10 is in an actuated position. When the operator releases the suction valve, spring 30 causes disposable suction valve 10 to return to the un-actuated position shown in FIG. 9a.

This procedure of aligning opening 35 with the suction pathway from the patient and sealing the suction cylinder of the endoscope, the negative pressure created by a suction pump or the like cause flow from the distal end of the endoscope towards the suction connection as shown in FIG. 9b can be accomplished with various suction valves and/or components, for example, those described in FIGS. 1-7. As a result, air and/or fluid may be suctioned from the distal end of the endoscope when disposable suction valve 10 is in an actuated position. When the operator releases the stem 15 of the suction valve 10, spring 30 causes disposable suction valve 10 to return to the un-actuated position shown in FIG. 9a.

Although the suction valve is designed to be used with an endoscope, it will be understood that other medical instruments can be used with the present suction valve or assembly. These instruments include, for example, colonoscopes, laparoscopes, bronchoscopes, or any medical instruments with a camera that requires suctioning.

In some embodiments, there is a method for manufacturing a disposable suction valve comprising: molding a stem; molding a flange for a resilient member; placing a bottom end of the stem through the center of the resilient member; placing the bottom end of the stem through a stem opening in the flange for the resilient member; and placing tabs of the flange for the resilient member into recessed apertures of the stem.

In some embodiments, there is a disposable suction valve wherein the stanchion or flange is monolithic with the boot (e.g., they are one piece).

In some embodiments, there is a suction valve assembly comprising: a stem comprising a first opening disposed along a longitudinal axis of the stem, and a second opening disposed transverse to the first opening, the first and second openings for allowing passage of air and/or fluid; a flange for a resilient member comprising at least one recess and/or projection configured to attach to the stem; the flange comprising an opening configured to receive the stem and allow movement of the stem in an upward and downward position relative to the flange; and the resilient member configured to contact the flange and the stem.

In some embodiments, there is a suction valve assembly comprising: a stem comprising a first opening disposed along a longitudinal axis of the stem, and a second opening disposed transverse to the first opening, the first and second openings for allowing passage of air and/or fluid; a flange for supporting a resilient member comprising at least one recess and/or projection configured to attach to the stem; the flange comprising an opening configured to receive the stem and allow movement of the stem in an upward and downward position relative to the flange; and the resilient member configured to contact the flange and the stem.

Figure 10:
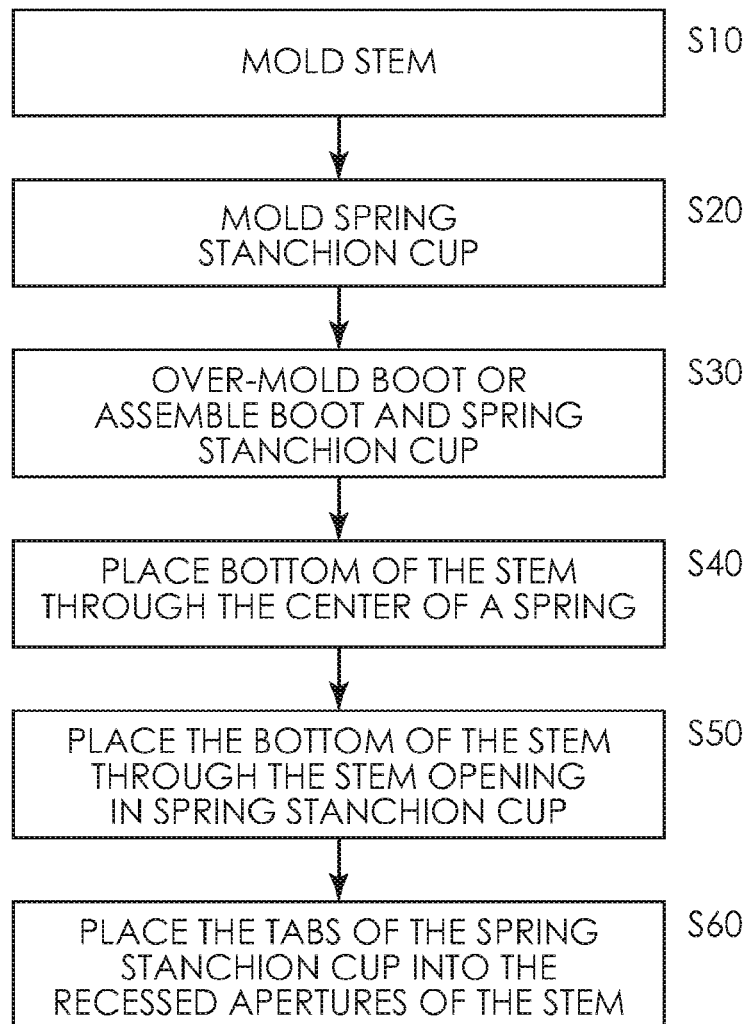
FIG. 10 illustrates a flow chart of an embodiment of a manufacturing process for a disposable suction valve.

FIG. 10 illustrates a flow chart of a manufacturing process for a disposable suction valve. In contrast to disposable suction valves, a re-usable suction valve may include metal components that are suitable for repeated cleaning, disinfection, and sterilization. These metal components may require more costly manufacturing and complicated assembly than the components of a disposable suction valve. For example, metal components may manufactured by precision machining/grinding, threading, stamping, machine pressing, or the like. Further, during assembly, the metal components may need to be welded together, glued using an adhesive, or the like. These steps may complicate manufacturing and increase cost.

A disposable suction valve provides a low cost manufacturing and simplified assembly process, thereby significantly reducing the cost of suction valve. The low cost materials, manufacturing processes, and assembly process of disposable suction valves provides an alternative to utilizing costly re-usable suction valve. Further, disposable suction valves allow the number of components to be reduced.

In step S10, a stem is molded using a suitable molding process, such as injection molding or the like. In step S20, a spring stanchion cup is molded using a suitable thermoplastic processing techniques, such as, for example, injection molding, rotational molding, or the like, extrusion techniques (for example, extrusion, co-extrusion, multi-layer extrusion, and so forth) and casting.

Stem and spring stanchion cup are formed from a suitable material such as for example, polyurethane, polyurea, polyether(amide), PEBA, thermoplastic elastomeric olefin, copolyester, styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), ABS, MABS, silicone, or the like or combinations thereof. Stem and spring stanchion cup may be formed from a rigid material that is capable of withstanding forces exerted on a suction valve by an operator.

In another embodiment of the manufacturing process, the stem and spring stanchion may be formed by ultrasonically welding molded pieces. A boot may be molded or assembled onto spring stanchion cup in step S30. The boot may be injection molded, over molded on the spring stanchion cup, or molded using any suitable molding process. When boot is molded separately, the boot may also be assembled on the spring stanchion cup during step S30. The boot is formed from a suitable material or combination of material(s), such as rubber, plastic, polymeric material(s), or the like. In steps S40 and S50, the bottom of the stem is placed through the center of a spring and the stem opening in the spring stanchion cup. Next, spring stanchion cup tabs are placed into recess apertures of the stem in step S60 to complete the assembly of the disposable suction valve.

It will be recognized by one of ordinary skill in the art that numerous steps in the manufacturing process may be optional or may be performed in a different sequence than specifically shown. The scope of the manufacturing process is not limited to the particular sequence and steps discussed herein, except as expressly recited in the claims. For example, it should be noted that the boot may be provided at various steps in the manufacturing process. In other embodiments of the manufacturing process, the boot may be assembled onto spring stanchion cup as the last step in the manufacturing process. Further, the stem and the spring stanchion cup may be molded simultaneously or in a sequence different than shown.

The suction valve may be sterilizable. In various embodiments, one or more components of the suction valve are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of the device, including, but not limited to, gas sterilization, such as, for example, with ethylene oxide or steam sterilization.

In various embodiments, a kit is provided that may include additional parts along with the suction valve combined together to be used with the suction valve. The kit may include the suction valve device in a first compartment. The second compartment may include a canister holding the suction valve and any other instruments needed for the procedure. A third compartment may include gloves, drapes, wound dressings and other procedural supplies for maintaining sterility, as well as an instruction booklet. A fourth compartment may include additional cannulas and/or needles. A fifth compartment may include an agent for radiographic imaging. Each device may be separately packaged in a plastic pouch that is radiation sterilized. A cover of the kit may include illustrations of the use of the device and a clear plastic cover may be placed over the compartments to maintain sterility.

Implementations described herein are included to demonstrate particular aspects of the present disclosure. It should be appreciated by those of skill in the art that the implementations described herein merely represent exemplary implementation of the disclosure. Those of ordinary skill in the art should, in light of the present disclosure, appreciate that many changes can be made in the specific implementations described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure, which is defined in the following claims.

From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure, which is defined in the following claims.

What is claimed is:

1. A method for manufacturing a disposable suction valve comprising: molding a stem; molding a spring stanchion; placing an end of the stem through the center of a spring; placing the end of the stem through a stem opening in the spring stanchion; and placing the spring stanchion into a first recessed aperture of the stem such that the stem engages the spring stanchion, the first recessed aperture configured to define the bounds of movement for the stem, wherein the stem further comprises a second recessed aperture between a first opening and a second opening of the stem, the second recessed aperture being disposed about the stem.

2. A method of claim 1 further comprising: over-molding a boot on the spring stanchion or over-molding the boot onto the spring stanchion.

3. A method of claim 2, wherein (i) the stem is color coded or (ii) a sealing ledge on the boot creates a seal against a button head of the stem.

4. A method of claim 1, wherein (i) the stem provides an O-ring or an alternate sealing device to assure an air-tight seal within a suction port or (ii) the stem provides a sealing means to assure an air-tight seal within a suction port or the stem.

5. A method of claim 1, wherein (i) the stem has a diameter that assures an air-tight seal within a suction port or (ii) a portion of the stem below the opening is removed such that a length of the stem is reduced.

6. A suction valve assembly comprising: a stem comprising a first opening disposed along a longitudinal axis of the stem, and a second opening disposed transverse to the first opening, the first and second openings for allowing passage of air and/or fluid; a spring stanchion comprising an opening configured to receive the stem and allow movement of the stem in an upward and downward position relative to the spring stanchion; and a spring configured to contact the spring stanchion and the stem, wherein the stem comprises a first recessed aperture to engage the spring stanchion, configured to define the bounds of movement for the stem, and the stem further comprises a second recessed aperture between the first opening and the second opening, the second recessed aperture being disposed about the stem.

7. A suction valve assembly according to claim 6, further comprising a boot configured to be attached to the spring stanchion and stem and configured to be contacted by the stem when the stem is moved in a downward position.

8. A suction valve assembly according to claim 6, further comprising a boot configured to be attached to the spring stanchion and to be contacted by the stem when the stem is moved in a downward position.

9. A suction valve assembly according to claim 8, wherein the boot comprises a ledge configured to receive a button head portion of the stem to provide an air tight seal when the top portion of the stem contacts the ledge of the boot.

10. A suction valve assembly according to claim 8, wherein the stem has a diameter that is concentric to the diameter of the boot to assure an airtight seal within a suction port of a medical device.

11. A suction valve assembly according to claim 10, wherein the medical instrument comprises an endoscope.

12. A suction valve assembly according to claim 6, wherein the spring stanchion further comprising a boot configured to be attached to the spring stanchion and to be contacted by the stem when the stem is moved in a downward position.

13. A suction valve assembly according to claim 6, wherein the stem is configured to slidably receive the spring stanchion and the stem being movable in a downward position on application of downward pressing force.

14. A suction valve assembly according to claim 6, wherein the opening in the spring stanchion is disposed in a center of the spring stanchion and the spring stanchion comprises a ledge to receive a first end of the spring and the stem comprises a ledge to receive the second end of the spring.

15. A suction valve assembly according to claim 6, wherein the suction valve assembly comprises a stem insert disposed in the first opening of the stem, the stem insert configured to prevent air passage out of the first opening.

16. A suction valve assembly according to claim 6, wherein (i) the stem comprises a plurality of points at one end, and a top portion or a button head at an opposite end configured to be contacted by a finger; (ii) the stem comprises a projection comprising a sealing member to assure a proper seal within a suction port of a medical device; and (iii) the stem comprises an O-ring attached thereto to assure a proper seal within a suction port of a medical device.

17. A suction valve assembly according to claim 6, wherein the stem, and spring stanchion comprise disposable thermoplastic material.

18. A suction valve assembly according to claim 6, wherein the first opening contacts the second opening, and when the stem is pressed in a downward direction, the second opening aligns with a suction channel of a medical instrument and allows passage of air and/or fluid to a suction connection.

19. A suction valve assembly according to claim 6, wherein the suction valve assembly is disposable.

20. A suction valve assembly according to claim 6, wherein the suction valve assembly is used in an endoscopic procedure.

21. A suction valve assembly according to claim 6, wherein the spring stanchion comprises a cutout.

22. A suction valve assembly according to claim 6, wherein the second recessed aperture is disposed about a portion of the stem.

23. A suction valve assembly according to claim 6, wherein the second recessed aperture is disposed around a portion of the stem.

\* \* \* \* \*